US00PP25308P3

(12) United States Plant Patent
Labonte et al.

(10) Patent No.: US PP25,308 P3
(45) Date of Patent: Feb. 24, 2015

(54) SWEETPOTATO PLANT NAMED 'LA04-175'

(50) Latin Name: ***Ipomoea batatas* (L.) Lam.**
Varietal Denomination: LA04-175

(71) Applicant: Board of Supervisors of Louisiana State University and Agricultural and Mechanical College, Baton Rouge, LA (US)

(72) Inventors: Don R. Labonte, Baton Rouge, LA (US); Arthur Q. Villordon, Monroe, LA (US); Tara Parker Smith, Chase, LA (US); Christopher A. Clark, Baton Rouge, LA (US)

(73) Assignee: Board of Supervisors of Louisiana State University and A&M College Through The LSU Ag Center, Baton Rouge, LA (US)

( * ) Notice: Subject to any disclaimer, the term of this patent is extended or adjusted under 35 U.S.C. 154(b) by 21 days.

(21) Appl. No.: 13/986,357

(22) Filed: Apr. 23, 2013

(65) Prior Publication Data

US 2014/0317801 P1 Oct. 23, 2014

(51) Int. Cl.
*A01H 5/06* (2006.01)

(52) U.S. Cl.
USPC ..... Plt./258

(58) Field of Classification Search
CPC ..... A01H 5/00; A01H 5/06
USPC ..... Plt./258
See application file for complete search history.

*Primary Examiner* — June Hwu
*Assistant Examiner* — Keith Robinson
(74) *Attorney, Agent, or Firm* — James C. Carver

(57) ABSTRACT

A new variety of sweetpotato, identified as 'LA04-175', is disclosed having disease resistance to both *fusarium* wilt, *Streptomyces* soil rot, and southern root-knot nematode; an orange flesh and red skin, and high yield characteristics.

3 Drawing Sheets

SUMMARY OF THE INVENTION

Genus and species name: This new and distinct sweetpotato variety, *Ipomoea batatas* (L.) Lam., demonstrates superior disease resistance to southern root-knot nematode and exhibits an orange flesh. It also demonstrates a red skin in comparison to 'Beauregard'.

Variety denomination: This new and distinct sweetpotato variety is identified as 'LA04-175', and is characterized by an orange flesh, high yield, consistent shape, and a red skin.

This invention pertains to a new and distinct variety of sweetpotato.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and no eyes, and are not derived from an underground branch. Sweetpotatoes do not form tubers.

BRIEF DESCRIPTION OF THE DRAWINGS

The file of this patent contains at least one photograph executed in color. Copies of this patent or patent application with color drawing(s) will be provided by the Patent and Trademark Office upon request and payment of the necessary fee.

FIG. 1 is a color photograph of the fleshy root form of the novel variety of sweetpotato identified as 'LA04-175'.

FIG. 2 is a color photograph of the fleshy root form of the sweetpotato variety identified as 'Beauregard'.

FIG. 3 is a color photograph of the canopy biomass of the variety of sweetpotato identified as 'LA04-175'.

DETAILED BOTANICAL DESCRIPTION

This new variety of sweetpotato, named 'LA04-175', resulted from an open pollinated cross performed in 2003 to the female parent 'NC96-61' (not patented). The male parent was unknown. Three patented male parents ('L96-117'—U.S. Plant Pat. No. 15,038 P2; 'Bienville'—patented U.S. Plant Pat. No. 15,380 P3; 'Evangeline'—patented U.S. Plant Pat. No. 19,710 P3) were among the potential pollen sources in the crossing nursery. 'LA04-175' was developed to provide a variety with characteristics similar to 'Beauregard' (unpatented), but with a red skin. No other potential antecedent included in the population of potential parents possesses a similar red skin.

Plants of 'LA04-175' and 'Beauregard' can be differentiated. Adaxial veins of 'LA04-175' are red [2.5 R (red) P (purple) (3/4)]. 'Beauregard' has no red hue to veins. Color terminology used herein is in accordance with a 2003 MUNSELL® Book of Color (Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'LA04-175'.

LA04-175' roots were stored during the 2004/2005 winter at Chase, La. 'LA04-175' was planted the following spring (2005), resulting in approximately 8-10 sprouts per root. Cuttings from the sprouts were transplanted successfully for asexual reproduction. Asexual propagation of the new cultivar by cuttings has shown that the unique features of this new sweetpotato were stable and that the plant reproduced true to type in successive generations of asexual propagation. Plants described herein were 90 days in age from planting in full sun field plantings.

FIG. 1 depicts the fleshy root form of the 'LA04-175' sweetpotato. The skin is red and differs from the light to medium rose 'Beauregard', both at harvest and after several months of storage as shown in Table 1. MUNSELL® Book of Color values for skin and flesh for both 'LA04- 175' and 'Beauregard' storage roots after 6 months of storage are shown in Table 1. The 'Beauregard' sweetpotato is depicted in FIG. 2. The skin for both 'LA04-175' and 'Beauregard' was smooth. 'LA04-175' storage roots were elliptical without lobing, and tend to be more round than the longer 'Beauregard'. The 'LA04-175' cortex was 4.4 mm in depth and the color similar throughout. The flesh of 'LA04-175' is deep orange in comparison to the lighter flesh of 'Beauregard'.

TABLE 1

| Variable | Variety | Color |
|---|---|---|
| Skin | 'LA04-175' | 10 R (red) P (purple) 4/6 |
| | 'Beauregard' | 10 R (red) 6/6 |
| Flesh | 'LA04-175' | 5 Y (yellow) R (red) 7/10 |
| | 'Beauregard' | 2.5 Y (yellow) R (red) 7/8 |

FIG. 3 depicts the canopy biomass of 'LA04-175' sweetpotato. Stems of 'LA04-175' change from green [2.5 G (green) Y (yellow) (5/6)] at the apex to purple [2.5 R (red) P (purple) 2/8] 30-40 cm from the apex and extends to the crown of the roots. The 'LA04-175' canopy biomass appears similar to 'Beauregard'. The 'LA04-175' canopy architecture was 30 cm in height from the soil surface and 120 cm in a radial spread and slightly less than 'Beauregard'. The growth habit of the plant is typical for sweetpotato. Lateral vines arising from the primary plant begin spreading 3-4 weeks after planting and densely cover adjacent region. For 'LA04-175', two to three main vines arose from the main stem near the soil surface. The round stem giving rise to these vines was 1.0-1.5 cm in diameter; the 2-3 lateral round vines were 150 cm in length with diameters of about 0.6 cm at 65 cm from the base and diameters of about 0.6 cm at the first internode of the first fully developed leaf from the apex. Three to four round lateral branches arose from each of the main vines. Vines measuring 120 cm are glabrous, smooth to the touch, pliable up to 90° before tissue damage midvine, and resist complete breakage up to 180° mid vine. Vines climb amongst themselves and reach 30 cm in height. At the first internode from the apex, the internode length was about 6 cm between the first and second fully developed leaves. Internode lengths for other sections of the vine averaged about 8 cm. Internodes vary from 0.63 cm to 0.70 cm in diameter. Unfolded immature leaves were dark green with a bronze cast [10 G (green) Y (yellow) (2/4)] for the upper and green for the lower surface [7.5 G (green) Y (yellow) (4/4)], which change gradually over one to two nodes from the apex to a green upper surface [5 G (green) Y (yellow) (3/4)] to a green lower surface [5 G (green) Y (yellow) (5/6)]. Mature leaves at five nodes from the apex had an acute apex and mostly a cordate base and a smooth leaf margin, and smooth upper and lower surface. Mature leaves were about 9 cm long and 10 cm wide. Abaxial and adaxial veins were purple [2.5 R (red) P (purple) (3/4)] and main veins radiate from the junction of the petiole to the leaf margin. Secondary and tertiary veins are in a typical net venation pattern. The petiole was green [7.5 G (green) Y (yellow) (4/4)]. A red [2.5 R (red) P (purple) (3/4)] marking was at the base of the leaf junction with the petiole. The petiole was 13 cm long at five nodes from the apex, and 3 mm in diameter at 5 cm from the leaf junction. The dormant nodal meristem was green [2.5 G (green) Y (yellow) (5/6)] and becomes purple [2.5 R (red) P (purple) 2/8] 30-40 cm from the apex and extends to the crown of the roots.

A typical inflorescence of 'LA04-175' displayed two clusters of six flowers per peduncle. Peduncles were green [7.5 G (green) Y (yellow) (4/2], about 20 cm long, and about 3 mm in diameter. Individual flowers were about 4.1 cm long from the base of the calyx, and the corolla was 4 cm wide at the opening and extends 3 cm from the top of the calyx. The fused flower petals formed a pentagonal pattern with smooth edges. The inner throat of the corolla appeared purple [7.5 P (purple) (4/6)]. The inner and outer limbs of the corolla (corollas outermost area, distal from the calyx) were light purple [10 P (purple) (6/4)]. The five sepals comprising the calyx were elliptic with a cordate apex and appeared to be green [2.5 G (green) Y (yellow) (6/6)]; three of these sepals were about 13 mm long and 4 mm wide. Two other sepals (interspersed) were about 9 mm long and 3 mm wide. Sepal margins were smooth. Stigmata were about 1.6 cm long and appeared to be purple [7.5 R (red) P (purple) (4/6)] at the base before fading. Five stamens were inferior to the stigmata. A slight fragrance was present.

EXAMPLE 1

Tests Conducted

To confirm that 'LA04-175' was a new variety, controlled tests (e.g., pathogen responses and yield) were conducted in Baton Rouge, La. 'Beauregard' was selected for comparison because of its importance in commercial United States orange flesh sweetpotato acreage. Diseases that commonly affect the growth of sweetpotatoes were selected to test for pathogen responses in both varieties. Scions of 'LA04-175' and 'Beauregard' reacted similarly to most diseases evaluated in the controlled tests. 'LA04-175' and 'Beauregard' were intermediate to resistant for *Streptomyces* soil rot caused by *Streptomyces ipomoeae* (Person & W. J. Martin) Waksman & Henrici in tests conducted during June to October, 2006; June to October, 2012, and June to October, 2013. 'LA04-175' and 'Beauregard' were resistant to *Fusarium* wilt or stem rot caused by *Fusarium oxysporum* Schlect. f. sp. *batatas* (Wollenw.) Snyd. & Hans in tests conducted in June, 2006; July, 2012, July, 2013, and May to June, 2014.

Nematode reproduction was measured in greenhouse tests in July to August, 2012; July to August, 2013, May to July, 2014. LA04-175' was highly resistant while 'Beauregard' was susceptible to southern root-knot nematode, *Meloidogyne incognita* (Kofoid & White 1919) Chitwood 1949.

'LA04-175' did not appear to show any novel insect resistance.

To determine yield production, complete-block trials using three to four replications of 'LA04-175' and 'Beauregard' each were conducted in 2005, 2009, 2010, 2011, and 2012 in areas of Louisiana and California likely to produce 'LA04-175'. 'LA04-175' and 'Beauregard' sweetpotato plants were transplanted in randomized complete-block trials at 31 cm spacings. Each block/plot was fertilized with approximately 280 Kg per hectare of a mixed fertilizer comprising 13% N, 13% $P_2O_5$, and 13% $K_2O$ in Louisiana and 7.3 Metric Tons per Hectare ($MT \cdot ha^{-1}$) of compost in California. 'LA04-175' was compared to 'Beauregard' at transplanting dates beginning in May-June. Average yields were measured for the following grades of roots: U.S. #1 (51-89 mm in diameter, 76-229 mm long); Canner (25-51 mm in diameter, 51-178 mm long); and Jumbo (larger than U.S. #1 in diameter, length or both, and without objectionable defects). A typical marketable root of 'LA04-175' was 180-190 mm long, 60-70 mm in diameter, with mostly round-elliptic in shapes. The base or distal end tended to be more elongated in comparison to slightly rounder apex (proximal end). U.S. #1 roots typically weighed 150-190 g.

An early-season transplanting date trial was conducted at Macon Ridge, La. in 2005. 'LA04-175' and 'Beauregard' were transplanted on May 27, 2005, and harvested on Sep. 30, 2005 (126 days after planting). Average yields, measured as Metric Tons per Hectare ($MT \cdot ha^{-1}$), are shown in Table 2.

TABLE 2

| Selection | US#1† | Canners† | Jumbos† | TMY‡† |
|---|---|---|---|---|
| 'LA04-175' | 25.1a | 5.35a | 5.58a | 36.0a |
| 'Beauregard' | 24.0a | 3.14a | 18.83a | 46.0a |

†Average yields in $MT \cdot ha^{-1}$ of varieties followed by a common letter do not differ significantly ($P < 0.05$) according to Duncan's Multiple Range Test.
TMY‡ = total marketable yield An early-season transplanting date trial was also conducted at Grand Prairie, La. on May 31, 2012, and harvested on Oct. 4, 2012 (126 days after planting). Average yields ($MT \cdot ha^{-1}$) by grade of 'LA04-175' and 'Beauregard' are shown in Table 3.

TABLE 3

| Selection | US#1† | Canners† | Jumbos† | TMY‡† |
|---|---|---|---|---|
| 'LA04-175' | 22.0a | 9.1a | 1.3a | 32.4a |
| 'Beauregard' | 21.3a | 8.9a | 1.2a | 31.4a |

†Average yields in $MT \cdot ha^{-1}$ of varieties followed by a common letter do not differ significantly ($P < 0.05$) according to Duncan's Multiple Range Test.
TMY‡ = total marketable yield An early-season transplanting date trial was also conducted at Livingston, Calif. on May 27, 2010, and harvested on Oct. 10, 2010 (148 days after planting). Average yields ($MT \cdot ha^{-1}$) by grade of 'LA04-175' and 'Beauregard' are shown in Table 4.

TABLE 4

| Selection | US#1† | Canners† | Jumbos† | TMY‡† |
|---|---|---|---|---|
| 'LA04-175' | 12.2a | 5.0a | 8.0b | 25.3a |
| 'Beauregard' | 11.4a | 4.8a | 12.7a | 28.8a |

†Average yields in $MT \cdot ha^{-1}$ of varieties followed by a common letter do not differ significantly ($P < 0.05$) according to Duncan's Multiple Range Test.
TMY‡ = total marketable yield A mid-season transplanting date trial was also conducted at Livingston, Calif. on Jun. 2, 2011, and harvested on Oct. 25, 2011 (145 days after planting). Average yields ($MT \cdot ha^{-}1$) by grade of 'LA04-175' and 'Beauregard' are shown in Table 5.

TABLE 5

| Selection | US#1† | Canners† | Jumbos† | TMY‡† |
|---|---|---|---|---|
| 'LA04-175' | 22.0a | 10.9a | 7.9b | 40.9a |
| 'Beauregard' | 14.1b | 14.1a | 13.0a | 39.4a |

†Average yields in $MT \cdot ha^{-1}$ of varieties followed by a common letter do not differ significantly ($P < 0.05$) according to Duncan's Multiple Range Test.
TMY‡ = total marketable yield An early-season transplanting date trial was also conducted at Livingston, Calif. on May 28, 2009, and harvested on Oct. 28, 2009 (153 days after planting). Average yields ($MT \cdot ha^{-1}$) by grade of 'LA04-175' and 'Beauregard' are shown in Table 6.

TABLE 6

| Selection | US#1† | Canners† | Jumbos† | TMY‡† |
|---|---|---|---|---|
| 'LA04-175' | 31.8a | 5.5a | 22.6b | 53.6b |
| 'Beauregard' | 16.1b | 4.1a | 43.7a | 63.9a |

†Average yields in $MT \cdot ha^{-1}$ of varieties followed by a common letter do not differ significantly ($P < 0.05$) according to Duncan's Multiple Range Test.
TMY‡ = total marketable yield As shown in Tables 2-6, 'LA04-175' produced yields comparable to, and exceeding 'Beauregard' in trials at various planting dates. Yield in comparison to 'Beauregard' in heavier silt loam soils (Tables 2, and 3) were similar to outcomes in lighter, sandy loam soils (Tables 4, 5 and 6). Replicated plots at other farms and have shown 'LA04-175' has yield declines within norms in poor environments. 'LA04-175' had harvestable roots approximately 100-110 days after planting in California which is a typical development time for sweetpotatoes and slightly earlier in comparison to 'Beauregard'. It is comparable to 'Beauregard' in Louisiana. The yield of Jumbo grade is normally indicative of earliness; however, 'LA04-175' tends to have less jumbo yield in comparison to 'Beauregard'. Yield in 15 other plots (data not shown) in California in years 2009, 2011, and 2012 showed consistent performance for U.S. #1 grade [23 $MT \cdot ha^{-1}$ average in 2009 (7 plots); 41 $MT \cdot ha^{-1}$ average in 2011 (1 plot); 25 $MT \cdot ha^{-1}$ average in 2012 (7 plots)]. In total, this data reflects consistent high yield characteristics for 'LA04-175'.

Sugar profiles for baked 'LA04-175' and 'Beauregard' are shown in Table 7. For this 2012 test, roots were stored for three months after which they were baked at 190° C. for approximately 2.0 h. Sucrose content in baked 'LA04-175' was higher in comparison to baked 'Beauregard'; maltose was the converse. Overall, 'LA04-175' had a lower total sugar content; however, a higher sucrose content compensates for a lower maltose and fructose content (less sweet sugars on a sucrose equivalency). Dry matter for 'LA04-175' is similar (22.1%) in comparison to 'Beauregard' (21.3%). These results demonstrate a similar level of sweetness and moistness for 'LA04-175' and 'Beauregard'.

TABLE 7

| Selection | Fructose‡ | Glucose‡ | Sucrose‡ | Maltose‡ | Total sugars†‡ |
|---|---|---|---|---|---|
| 'LA04-175' | 0.39 | 0.48 | 4.41 | 2.67 | 7.95 |
| 'Beauregard' | 0.96 | 1.20 | 2.30 | 4.89 | 9.35 |

†Total sugars = fructose + glucose + maltose + sucrose
‡$mg \cdot g^{-1}$ fresh weight basis.

'LA04-175' should be a valuable commercial sweetpotato variety. 'LA04-175' produced plants (sprouts) comparable to 'Beauregard'. Days to harvest 'LA04-175' is earlier in California by ~10 days in comparison to 'Beauregard' for the U.S. #1 grade; days to harvest in Louisiana are comparable. 'LA04-175' exhibited a higher sucrose content in comparison to 'Beauregard'.

We claim:

1. A new and distinct variety of *Ipomoea batatas* plant named 'LA04-175' as described and illustrated in the specification herein.

* * * * *

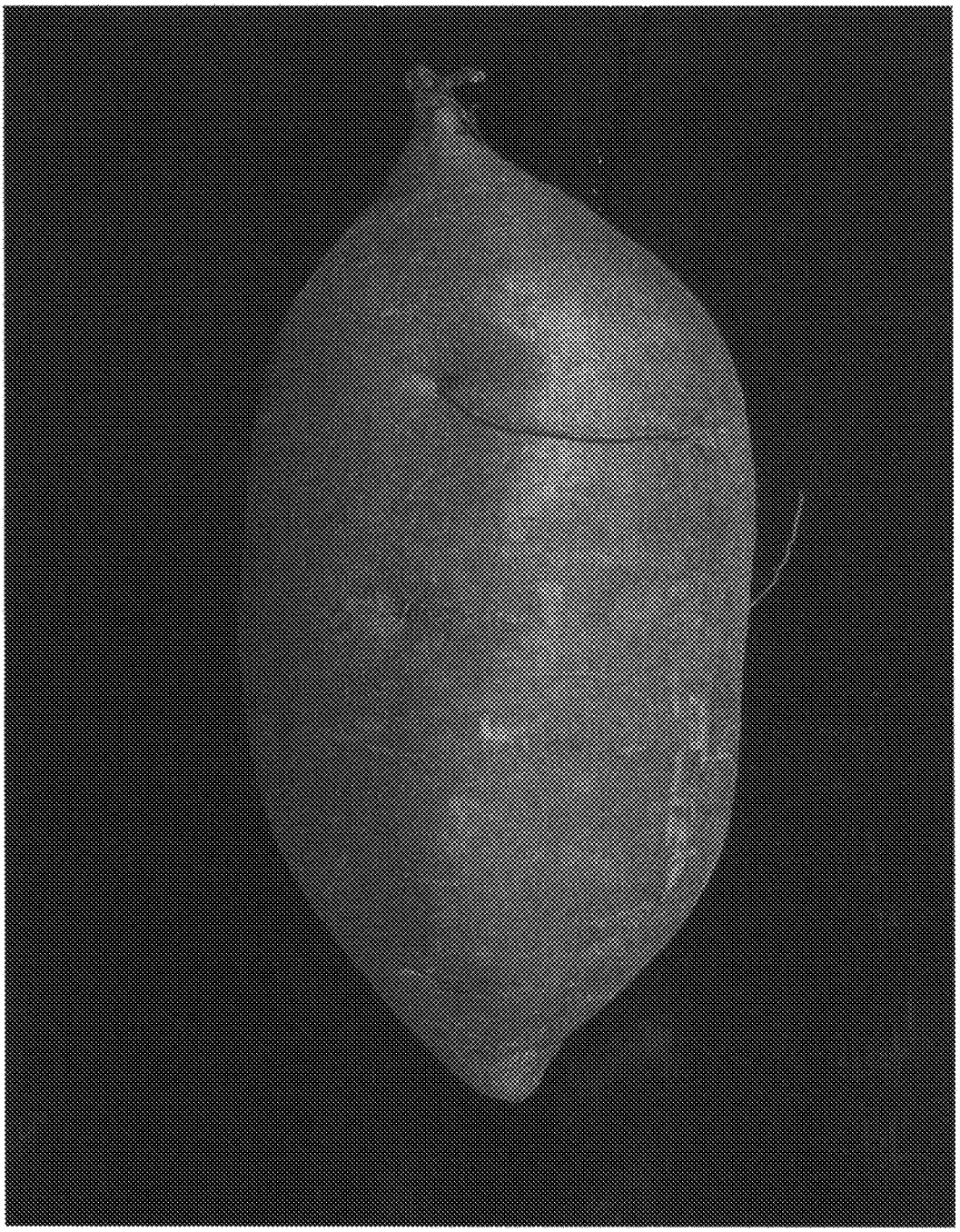

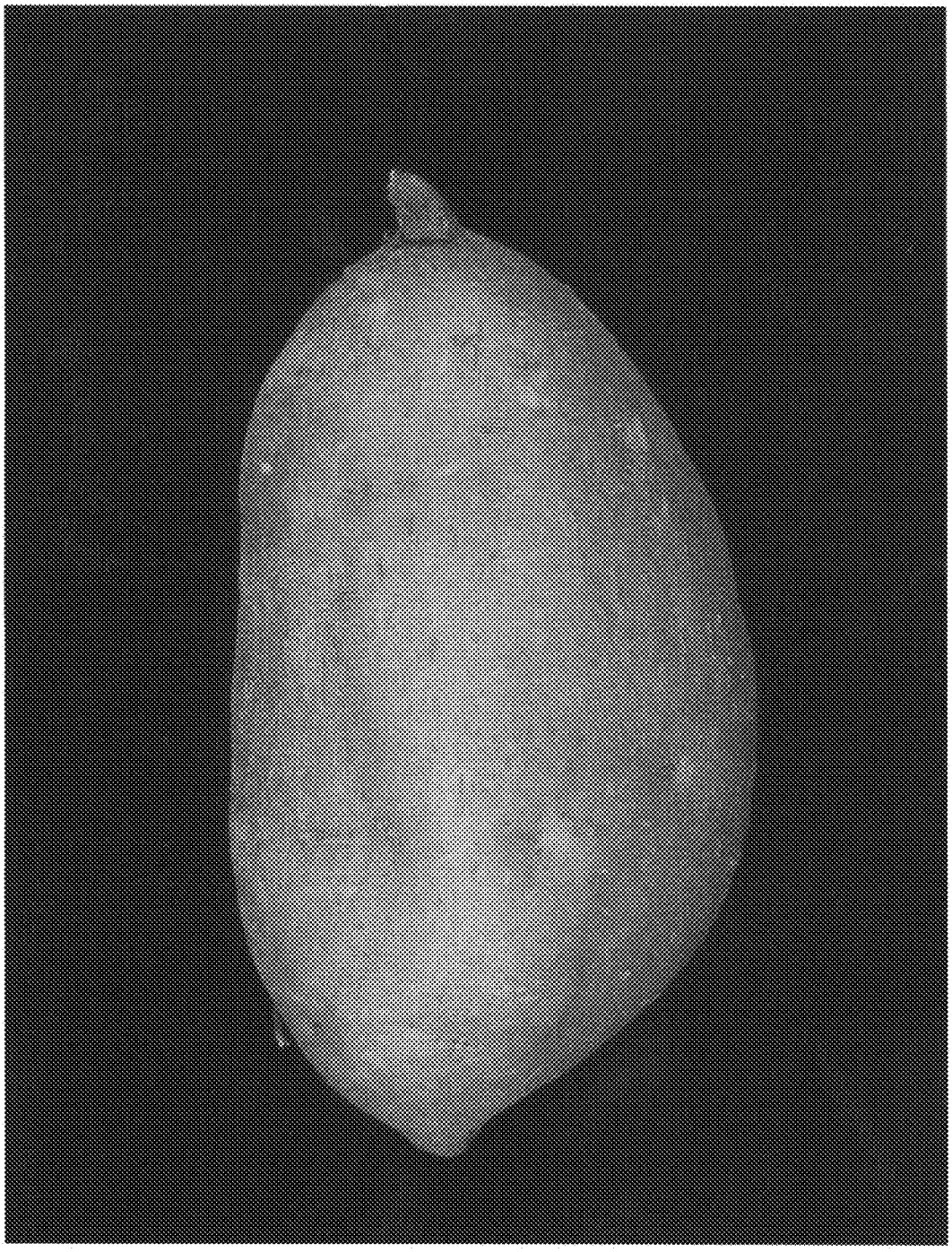

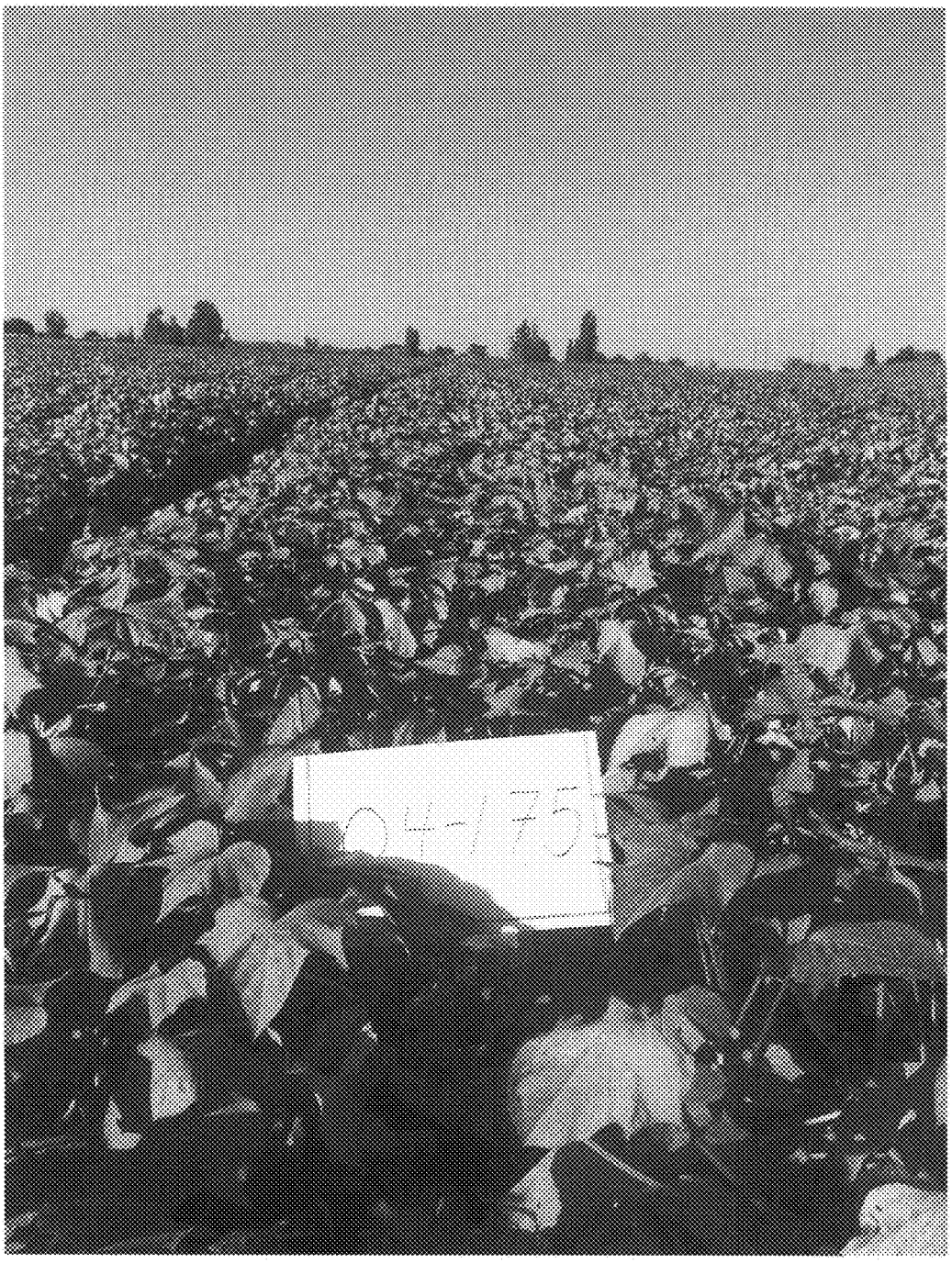
04-175